(12) United States Patent
Vangeloff (10) Patent No.: US 10,413,438 B1
(45) Date of Patent: Sep. 17, 2019

(54) DORSAL SPINE SUPPORT DEVICE

(71) Applicant: Don Edward Vangeloff, Redondo Beach, CA (US)

(72) Inventor: Don Edward Vangeloff, Redondo Beach, CA (US)

( * ) Notice: Subject to any disclaimer, the term of this patent is extended or adjusted under 35 U.S.C. 154(b) by 929 days.

(21) Appl. No.: 14/799,249

(22) Filed: Jul. 14, 2015

Related U.S. Application Data (60) Provisional application No. 62/024,837, filed on Jul. 15, 2014.

(51) Int. Cl.
*A61F 5/02* (2006.01)
*A61F 5/30* (2006.01)

(52) U.S. Cl.
CPC ............... *A61F 5/026* (2013.01); *A61F 5/30* (2013.01)

(58) Field of Classification Search
CPC .. A61F 5/024; A61F 5/026; A61F 5/30; A61F 5/3784; A61F 5/05858; A41B 9/16; A41F 1/00; A41F 1/006; A41F 18/00; A41F 19/00; A41F 15/00; A41F 15/002; A41D 13/0512
USPC ....... 602/19; 128/869; 2/300, 310, 326–328, 2/333, 336; 450/85–86
See application file for complete search history.

(56) References Cited

U.S. PATENT DOCUMENTS

| | | | | |
|---|---|---|---|---|
| 5,120,288 A | * | 6/1992 | Sinaki | A63B 21/065 |
| | | | | 128/DIG. 19 |
| 5,498,233 A | * | 3/1996 | Stojanovic | A41D 13/0512 |
| | | | | 128/845 |
| 6,991,611 B2 | * | 1/2006 | Rhee | A61F 5/026 |
| | | | | 128/869 |
| 8,123,588 B2 | * | 2/2012 | Tyrer | A41C 3/0021 |
| | | | | 2/326 |
| 9,456,919 B2 | * | 10/2016 | Pollack | A61F 5/026 |
| 9,883,703 B2 | * | 2/2018 | Schultz | A61F 5/026 |
| 2010/0200329 A1 | * | 8/2010 | Johnson | A62B 35/0025 |
| | | | | 182/3 |
| 2014/0066973 A1 | * | 3/2014 | Mahoney | A61F 5/30 |
| | | | | 606/201 |

* cited by examiner

*Primary Examiner* — Kari K Rodriquez
*Assistant Examiner* — Camtu T Nguyen
(74) *Attorney, Agent, or Firm* — Knobbe Martens Olson & Bear LLP (57) ABSTRACT

A dorsal spine support device has a support element that is a single strap with a closure assembly. The single strap intersects itself in exactly three discrete locations. The single strap has a first end and a second end. The closure assembly has a buckle with a first portion and a second portion. The first portion of the buckle is connectable to and disconnectable from the second portion of the buckle. The first portion of the buckle can be secured to the first end of the single strap and the second portion of the buckle can be secured to the second end of the single strap. A pad can be positioned in a pouch. The pouch can be secured to the strap.

16 Claims, 11 Drawing Sheets

FIG. 11

DORSAL SPINE SUPPORT DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present invention generally relates to devices designed to apply pressure to, on and/or around the thoracic spine region. More particularly, the present invention relates to such devices that are configured for ease of adjustment and implementation.

Description of the Related Art

There is a need in the yoga and exercise industries for a solution to the problem of implementing a support that can assist with attaining a desired spinal posture during a session. The support should assist with attaining the desired posture while freeing the hands of the user to perform a variety of poses and positions. Moreover, it would be preferred if the support could be used without the assistance of a third party and it would be even more preferred if the support could be donned for wearing, adjusted and secured in position without the need for assistance by a third party.

SUMMARY OF THE INVENTION

The embodiments of the dorsal spine support device described herein are arranged and configured to achieve one or more of these goals, among others.

In some configurations, a dorsal spine support device comprises a support element. The support element consists of a single strap and a closure assembly. The single strap intersects itself in exactly three discrete locations. The single strap also comprises a first end and a second end. The closure assembly comprises a first portion and a second portion. The first portion of the closure assembly can be connectable to and disconnectable from the second portion. The first portion can be secured to the first end of the single strap and the second portion can be secured to the second end of the single strap.

In some configurations, the dorsal spine support further comprises a pouch that is attached to the single strap. In some such configurations, the pouch is adjustable in location along the single strap. In some such configurations, the pouch is removably connected to the single strap. In some such configurations, the pouch comprises one or more channels through which the single strap may pass. In some such configurations, the pouch is positioned at one of the exactly three discrete locations at which the single strap intersects itself.

In some configurations, the dorsal spine support device further comprises a pad. In some such configurations, the pad is sized and configured for insertion into the pouch. In some such configurations, the pad comprises a curved surface that is configured for contact with a body of a user. In some such configurations, the pad comprises a flat surface over which the strap passes such that the pad will be positioned between the strap and the body of the user. In some such configurations, the pad can have a soft, firm or very firm resilience. In some such configurations, the pad comprises two rounded surfaces arranged and configured to rest alongside a ridge of a spine of the body of the user. In some configurations, the pad comprises a recess that allows the pad to straddle the spine of the body of the user.

In some configurations, the strap comprises a relatively extensible portion and relatively inextensible portion. In some such configurations, two of the three distinct locations are lower on the body of the user in use and the extensible portion is between a first end of the strap and one of the two lower distinct locations. In some such configurations, the first portion of the closure assembly is adjustably located on a second end of the strap and the extensible portion is positioned only between the first end of the strap and the one of the two lower distinct locations.

In accordance with some features, aspects and advantages of the present invention, the dorsal spine support device can comprise a kit comprising two relatively smaller crisscross connectors, one relatively larger crisscross connector, a connector arranged and configured to join a first end of a strap to a second end of the strap, and one or more dorsal/upper-thoracic spine pads. In some such configurations, the kit also comprises a pouch that is sized and configured to receive the one or more dorsal/upper-thoracic spine pads and configured to attach to the one relatively larger crisscross connector. In some such configurations, the pouch is integrally formed as one unit with the one relatively larger crisscross connector. In some such configurations, the kit also comprises a strap.

BRIEF DESCRIPTION OF THE DRAWINGS

These and other features, aspects and advantages of the present invention will be described with reference to the following figures.

DETAILED DESCRIPTION OF THE PREFERRED EMBODIMENT

As discussed above, a dorsal spine support device 10 can be designed to enable one person to put it on, adjust one or more pad 12, 13, 14, 15, 17 (see FIGS. 7-11) of the dorsal spine support device 10 to a desired position, tighten a strap 16 of the dorsal spine support device 10 and easily fasten a closure member 18 of the dorsal spine support device 10 in front without assistance from anyone else. The closure member 18 can include an adjustable length element (e.g., a buckle) and, in the illustrated configuration, the closure member 18 has two portions that can be easily connected and disconnected to secure the dorsal spine support device 10 in position for hands-free use. The dorsal spine support device 10 advantageously enables the user to improve his or her posture while keeping their hands free. With the strap 16 and the one or more pad 12, 13, 14, 15, 17 in place, the user can perform a variety of yoga positions, dance positions, and the like with an improved positioning of the shoulders, spine, chest, and the heart. The user also can improve ergonomic positions through use of the strap 16 and the one or more pad 12, 13, 14, 15, 17.

With reference to the figures, the dorsal spine support device 10 generally comprises the elongated strap 16. In the illustrated configuration, the dorsal spine support device 10 uses only a single strap 16, which advantageously simplifies manufacture and use. The strap 16 can have any suitable configuration and can be formed of any suitable material.

In some configurations, the strap 16 can have a length of between eight feet and ten feet. With such a length, the strap 16 can be used by adults. In some configurations, the strap 16 can have a length of five feet to seven feet for use by more petite adults or children. Other suitable lengths also can be used. The strap 16 can have any suitable thickness and width. In some configurations, the strap 16 has a width of 1.5 inches.

Figure 5:
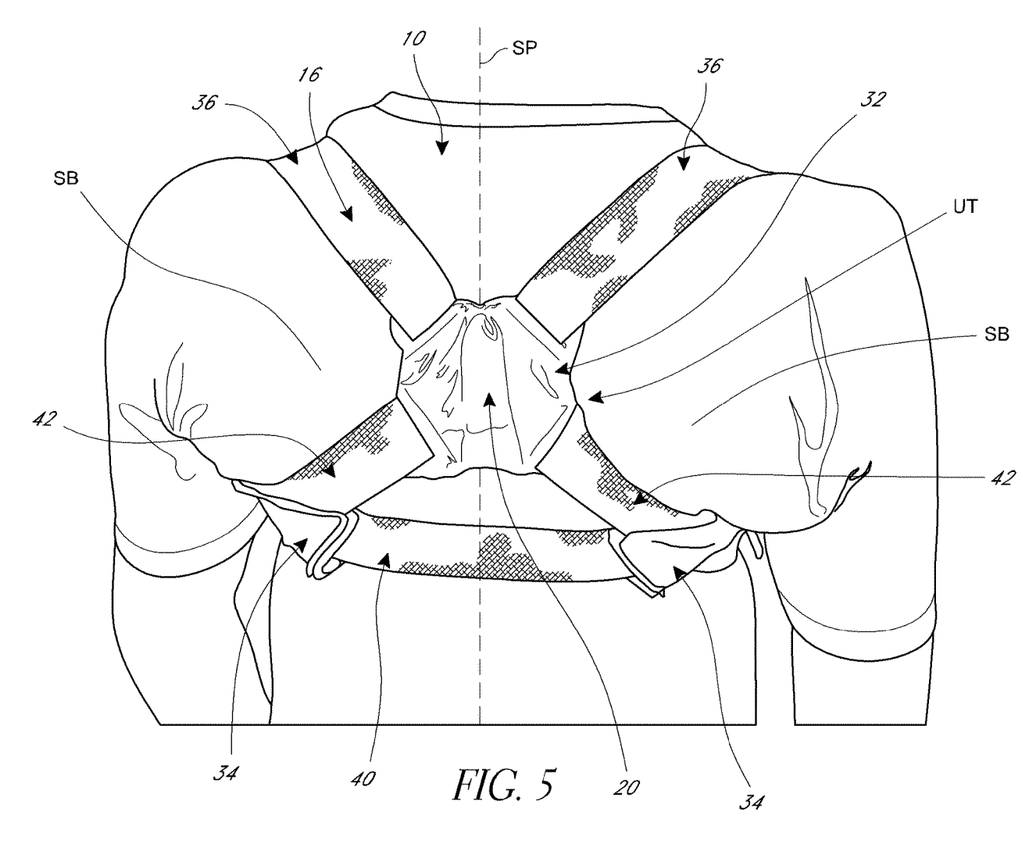
FIG. 5 is a rear view of the dorsal spine support device being worn.

A pouch 20 and/or pad 12, 13, 14, 15, 17 can be attached to the strap 16 such that the pouch 20 and/or pad 12, 13, 14, 15, 17 can be positioned between the shoulder blades SB when the strap is donned (see FIG. 5). As shown in FIG. 5, the pouch 20 can overlie the spine SP. In some configurations, a plurality of pouches 20 can be used. In some configurations, a plurality of pouches can be used with at least one pouch 20 being positioned on each side of the spine SP. In some configurations, the pouch 20 can have two or more compartments defined within the pouch. In the configuration shown in FIG. 3, the pouch 20 has a single compartment 22 defined within the pouch 20.

In the illustrated configuration, the pouch 20 includes a body-facing surface 21. The body-facing surface 21 will be in contact with the body of the user. As such, at least the body-facing surface 21 will be positioned between the strap 16 and the body of the user. The body-facing surface 21 can have any suitable configuration. In some configurations, the body-facing surface 21 may be formed of terrycloth, a quilted material, or soft-handed fabric or the like. Any other suitable materials also can be used.

Figure 3:
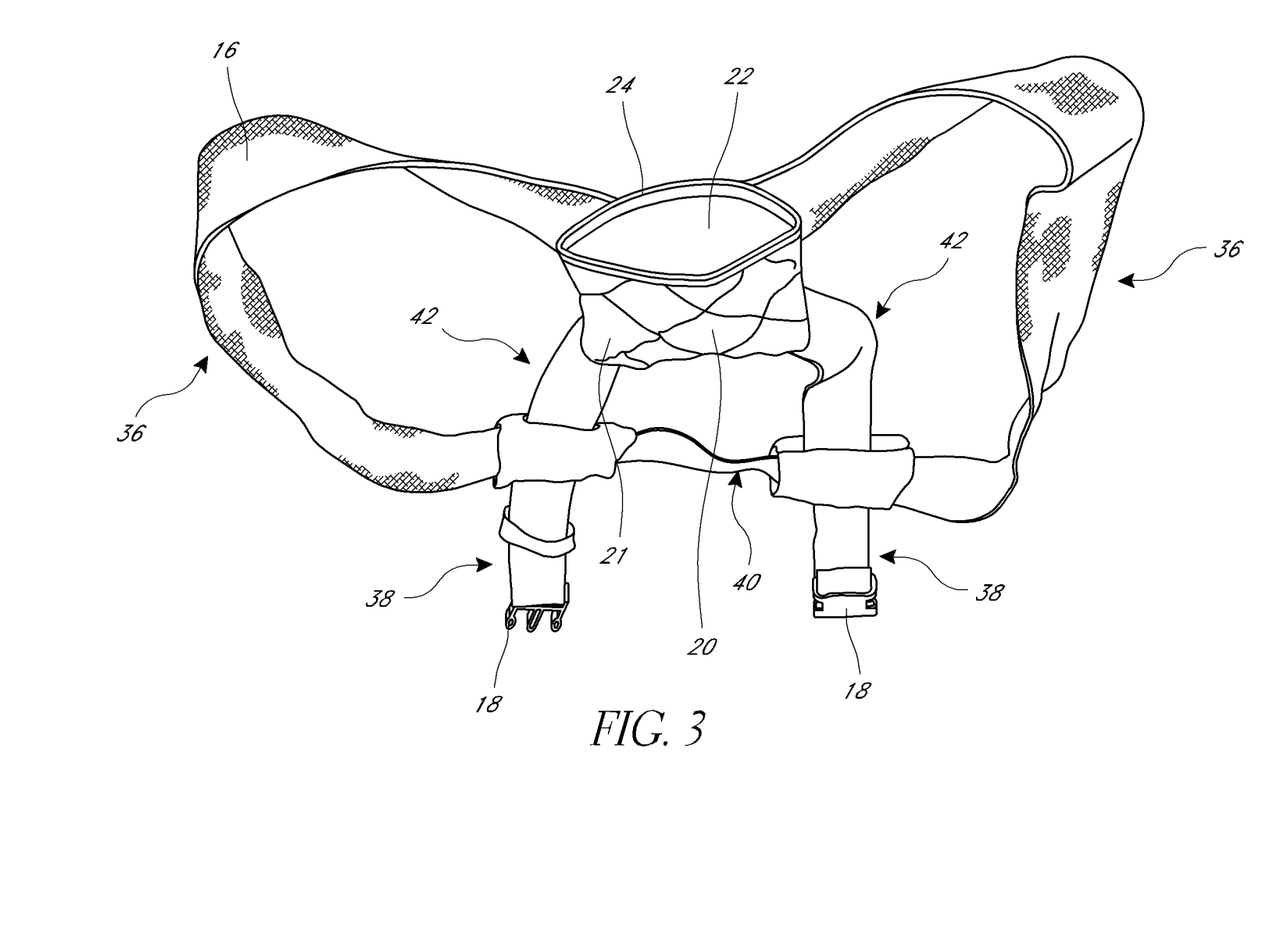
FIG. 3 is a view of the dorsal spine support device of FIG. 1 shown with a pouch in an opened position.
Figure 4:
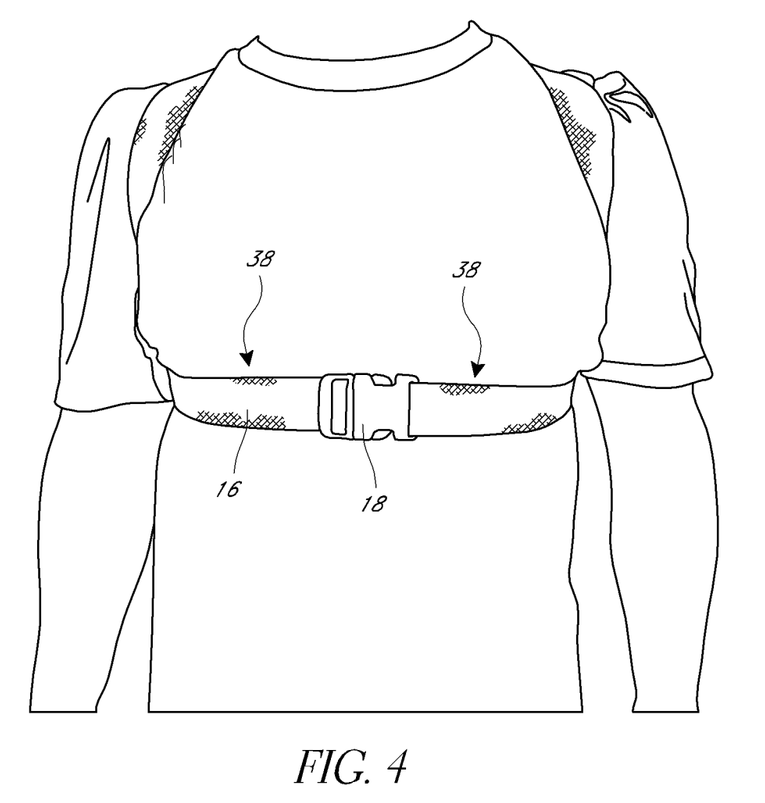
FIG. 4 is a front view of the dorsal spine support device being worn.

With reference to FIGS. 3 and 5, the pouch 20 and/or pad 12, 13, 14, 15, 17 can be configured to be positioned at least partially between the strap 16 and the body of the user. In some configurations, the pouch 20 and/or pad 12, 13, 14, 15, 17 can be positioned fully between the portion of the strap 16 that is in contact with the pouch 20 and/or pad 12, 13, 14, 15, 17 and the body of the user. In most configurations, the pouch 20 and/or pad 12, 13, 14, 15, 17 can be held in place relative to the body of the user by the strap 16. The position of the pouch 20 and/or the pad 12, 13, 14, 15, 17 can be adjustable along the length of the strap 16. The pouch 20 and/or pad 12, 13, 14, 15, 17 can be formed in any suitable manner and can be attached to the strap 16 in any suitable manner.

The pouch 20 that sits between the shoulder blades SB can be a pocket made of fabric with an opening 24 that can be opened and closed easily. In some configurations, the opening 24 opens in an upward direction when the dorsal spine support device 10 is properly positioned on the user. In some configurations, the opening 24 opens in any direction other than downward with the dorsal spine support device 10 is properly positioned on the user. In some configurations, the opening 24 extends through at least one end of the pouch 20. In some configurations, the opening 24 extends through only one end of the pouch 20. In some configurations, the opening 24 extends through a side of the pouch 20 such that the opening is positioned between the pad 12, 13, 14, 15, 17 and the body of the user.

The pouch 20 can hold the pad or pads 12, 13, 14, 15, 17 that get inserted into the pocket defined by the pouch 20. The pad or pads 12, 13, 14, 15, 17 can be fully inserted into the pouch 20 or at least a portion of the pad or pads 12, 13, 14, 15, 17 can extend beyond the pouch 20. In other configurations, the opening 24 is configured to remain open or at least not secured in a closed position. In some configurations, an opening through which the pad can be inserted into the pouch can be at least partially closed. In some configurations, the opening can be fully closed. In configurations in which the opening is designed to close, any suitable mechanism or technique can be used. For example, the opening 24 can be defined by two overlapping edges that can be parted to gain access to the pocket or cavity defined within the pouch 24. The opening 24 can be elastic such that it returns to an at least partially closed position when not being held open. In some configurations, a mechanical fastener or the like can be used to secure the opening in at least a partially closed state. The opening 24 can be secured in a closed or semi-closed position by a drawstring, by a drawstring that extends through a toggle, by one or more hook and loop fastener, by one or more button, by one or more snap, by one or more clasp, or in any other suitable configuration keeping in mind a desire to maintain the pad 12, 13, 14, 15, 17 within the cavity defined within the pouch 20 during use of the dorsal spine support device. In some configurations, the pouch 20 can be designed such that the pouch 20 greatly reduces or eliminates the likelihood of the pad or pads 12, 13, 14, 15, 17 falling out of the pouch 20 during use.

In some configurations, one or more channels 26 for the strap 16 can be formed on, along or at least partially inside of the pouch 20. In some configurations, the pouch 20 can be semi-permanently or permanently attached or sewn to one or more pieces of fabric. In some such configurations, the pouch 20 can be attached or sewn to two pieces of fabric. In some such configurations, the two pieces of fabric can be stitched together in a manner that defines the channels 26 as openings or sleeves that accommodate the strap 16 such that the strap can move along the channel in both directions. In some configurations, a single component (e.g., a single piece of fabric, leather or plastic, without limitation) can be used to define the openings or channels 26. For example, a single card shaped member can define passages through which the strap 16 is threaded to define channels 26 that control a relative positioning of two portions of the strap 16 that cross each other.

In the illustrated configuration, the openings or sleeves (i.e., the channels 26) allow a first end 28 and a second end 30 of the single strap 16 to crisscross at the location of the pouch 20, thereby creating a crisscross strap-loop connector 32. The connector 32 can be configured as part of the pouch 20 or can be secured to the pouch 20 or pad 12, 13, 14, 15, 17 in any suitable manner. For example, the pouch 20 can be removed or attached to the connector 32 as desired by the user such that the device 10 can be used with or without the pouch yet the connector 32 still functions to retain the strap in a desired crisscross pattern at a desired location. By way of a further example, where the pouch is omitted, the pad 12, 13, 14, 15, 17 can be configured for attachment to the connector 32 (e.g., using hook and loop fasteners, interlocking members or the like). The openings or sleeves of the connector 32 can be snug enough of a fit around the strap 16 to gently secure the strap 16 in the crisscross position even when not being worn. In other words, the friction between the strap 16 and the channels 26 is enough to maintain the location of the pouch 20 and/or pad(s) 12, 13, 14, 15, 17 relative to the strap 16. The connector 32 and/or the strap 16 can be configured to provide with sufficient resilience so that, when worn, the pouch 20 and/or pad(s) 12, 13, 14, 15, 17 can be slightly adjusted up or down the dorsal spine to achieve a desired positioning along the body of the user. In some configurations, the adjustments can be performed by the user. Of course, adjustments also can be made by an instructor or other third-party.

In some configurations, two smaller crisscross strap-loop connectors 34 can be used to connect shoulder loop portions 36 of the strap to a torso encircling portion 38 of the strap 16. In other words, two of the three intersections of the single strap can be formed by two smaller crisscross strap-loop connectors 34. The connectors 34 can be positioned along at least a portion 40 of the strap 16 that is arranged and configured to run horizontally across the back of the user (see FIG. 5) at a location just below the shoulder blades SB. The crisscross strap-loop connectors 34 also can be positioned along the two portions 42 of the strap 16 that extend between the pouch 20 and/or pad(s) 12, 13, 14, 15, 17 (or the third intersection of the three strap intersections) and the portion 40 of the strap 16 that is arranged and configured to extend horizontally across the back of the user at the location just below the shoulder blades SB. In other words, the illustrated dorsal spine support device 10 comprises a triangular configuration defined by the two non-horizontally extending portions 42 and the horizontally extending portion 40. In the illustrated configuration, each apex of the triangular configuration is defined by one of the connectors 32, 34. As shown in FIG. 5, when viewed from behind a user, the upper crisscross strap-loop is situated between the shoulder blades with the two smaller crisscross strap-loops being situated lower and apart with one below each shoulder blade.

The crisscross strap-loop connectors 34 can be formed in any suitable manner, including those described above with respect to the crisscross strap loop connector 32. The two smaller crisscross strap-loop connectors 34 also can be made from at least one piece of fabric, leather or plastic, for example but without limitation. In some configurations, the two smaller crisscross strap-loop connectors 34 can be formed from two pieces of fabric. The fabric can be stitched together in a manner that defines channels 44 (e.g., through the use of openings or sleeves). As with the upper crisscross strap-loop connector 32, the channels on these smaller crisscross strap-loop connectors 34 can be snug enough to hold the strap 16 in position but can be resilient enough for adjustment or comfort.

As described above, the pouch 20 can hold the pad or pads 12, 13, 14, 15, 17. In some configurations, the pad or pads 12, 13, 14, 15, 17 can be adjustable in position relative to the spine. For example, in some configurations, the pad or pads 12, 13, 14, 15, 17 can include the channels 26 such that the pouch 20 can be omitted. The pad or pads 12, 13, 14, 15, 17 can be removable and replaceable to vary the resilience and/or hardness of the pad 12, 13, 14, 15, 17.

Figure 9:
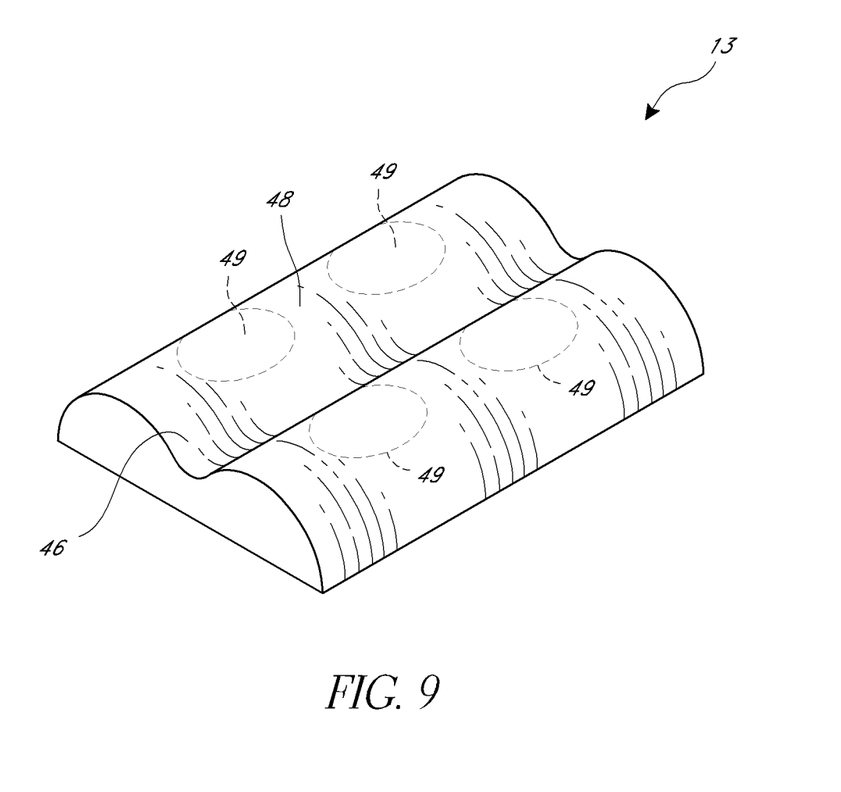

The pads 12, 13, 14, 15, 17 can be formed of any suitable material. In some configurations, a firm material, such as plastic or PVC, or a more resilient material, such as a rubber compound, can be used, for example but without limitation. In some configurations, the pads 12, 13, 14, 15, 17 can be adjustable. For example but without limitation, in some configurations, the pad or pads 12, 13, 14, 15, 17 can be pressurized by a fluid to change the resilience and/or hardness of the pad or pads 12, 13, 14, 15, 17. In some configurations, the degree of hardness of the pad or pads 12, 13, 14, 15, 17 can be adjusted or varied by replacing the pad or pads 12, 13, 14, 15, 17 with another similarly configured pad or pads 12, 13, 14, 15, 17 and/or a pad that is altogether different. Adjusting the degree of hardness can adjust the massage-like pressure. In some configurations, the pad or pads 12, 13, 14, 15, 17 can be adjustable in both position and degree of hardness. In some configurations, a single pad can have differing hardnesses in different regions of the same pad. For example, as shown in FIG. 9, the pad 13 can include regions 49 that are relatively more rigid or hard than the surround portions of the pad 13. The varying hardness, rigidity or resilience can be accomplished through the use of different materials or different qualities of a single material, for example but without limitation. Any other suitable technique can be used to provide a single pad with differing harnesses in different regions.

Figure 7:
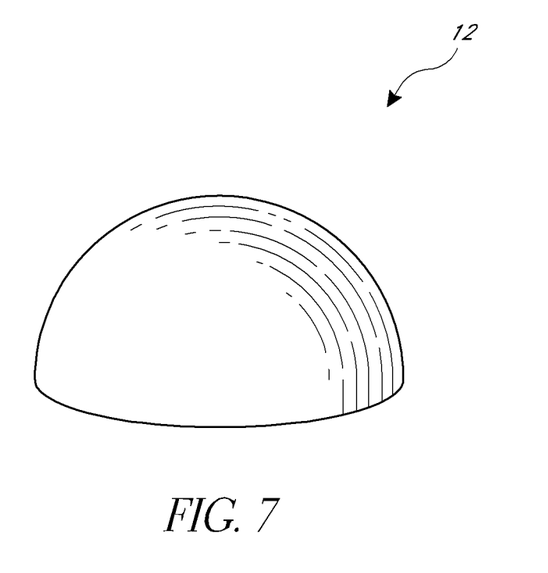
FIGS. 7, 8 and 9 are three representative pads usable with the dorsal spine support devices of FIGS. 1 and 6 by positioning one or more pads within the pouches of the dorsal spline support devices.
Figure 8:
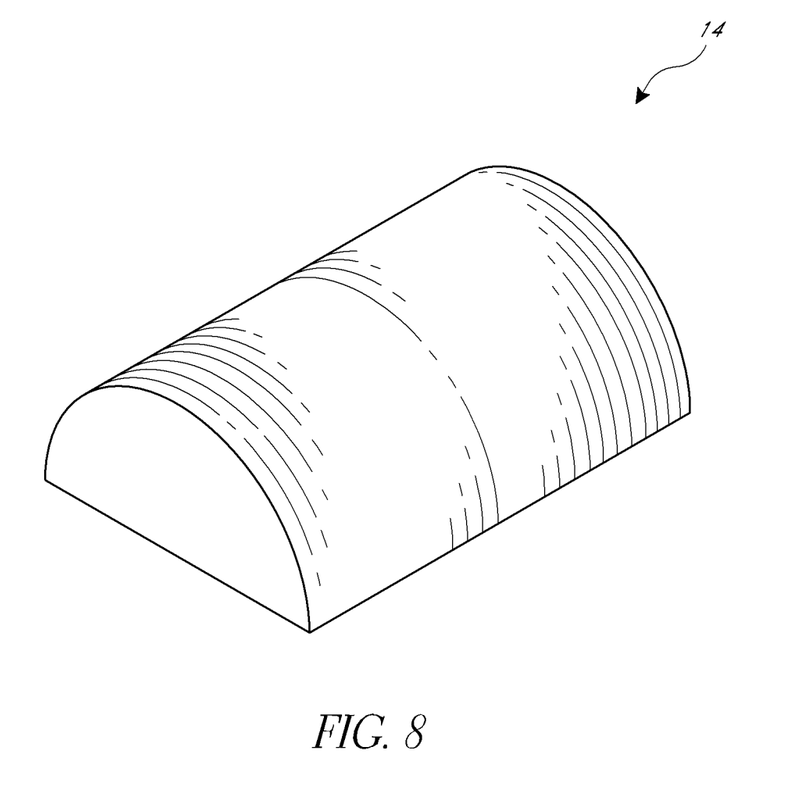

The pad or pads 12, 13, 14, 15, 17 can be designed to apply a degree of additional pressure to the dorsal/upper-thoracic spine region UT when the dorsal spine support device 10 is tightened. The effect of the presence of the pad or pads 12, 13, 14, 15, 17 is similar to having someone press down on that area of the spine SP when receiving a massage. The pads 12, 13, 14, 15, 17 can come in multiple designs, shapes and degrees of hardness. In some configurations, the pads 12, 14 are designed for use in applying direct pressure to the spine SP. In some such configurations, a hemispheric pad (e.g., looks like half of a baseball) can be used, as shown in FIG. 7. In some such configurations, a semi-cylindrical pad can be used, as shown in FIG. 8.

The pads 12, 13, 14, 15, 17 can be any suitable size. In some configurations, the pads 12, 13, 14, 15, 17 can be a few inches across (e.g., in diameter). In some such configurations, the pad 12, 13, 14, 15, 17 can be small enough to fit between the shoulder blades SB. In some such configurations, the pad 12, 13, 14, 15, 17 can be rounded with a rounded surface side being disposed against the body while fitting within the natural curvature of the spine and shoulder blades. In some such configurations, the pad 12, 13, 14, 15, 17 can have a flat side facing outward such that the crisscrossing portion of the strap can have a flat surface to bear against. In some configurations, the pouch 20 and/or the connector 32 can include a component that is sufficiently rigid to encourage transfer of force from the strap 16 to the pad or pads through the rigid component (e.g., a flat plate or the like).

In some configurations, a selection of pads can be provided. The selection of pads can have multiple levels of hardness. In some configurations, the pads can have three levels of hardness: (1) very firm—similar to baseball or lacrosse ball; (2) firm—similar to tennis ball or foam rubber ball (e.g., foam rubber baseball); and (3) soft—similar to stress-ball or easily squeezable ball. The level of firmness used in any particular situation may be based upon the user and the preference of, comfort of and/or use by the user. It is likely that people who already are athletic to a degree or have a larger build around their shoulders may desire a firm or very firm pad in order to feel more of the pressure effect while those with a slighter frame may achieve the same pressure effect with the soft pad. Also, if wearing the device for shorter periods of time, such as when practicing certain postures during a 30-minute yoga class or dance class, a more firm pad may be desired. On the other hand, if the user will be wearing the device for longer periods (e.g., more than 30 minutes), a softer pad may be preferred regardless of body type.

Some people have a spine that is close to the surface of the skin or that is sensitive to pressure due to injury, preference or other factors. In addition, some people may feel direct pressure on the spine to be uncomfortable or painful. Yet these same people may still want the press of their thoracic spine moving forward and really opening their chest. In some configurations, the user may prefer two pads separated by a gap. In some configurations, the gap can be between ½ inch and ¾ inch. In such configurations, the two pads can press against the back while straddling the ridge of the spine.

In some such configurations, the pads 12, 13, 14, 15, 17 can be small enough to fit between the shoulder blade SB and the spine SP. In some such configurations, the pad 12, 13, 14, 15, 17 can have a flat side facing outward such that the cross-crossing portion of the strap 16 can have a flat surface to bear against. In some configurations, the pouch 20 and/or the connector 32 can include a component that is sufficiently rigid to encourage transfer of force from the strap 16 to the pad or pads through the rigid component (e.g., a flat plate or the like). In some configurations, the pads can have a rounded body-contacting surface over at least a portion of the pads. In some configurations, the pads can be semi cylindrical or hemispherical, for example but without limitation. The two pads can be formed of a firm material, such as plastic or PVC, or a more resilient material, such as a rubber compound, can be used, for example but without limitation. In some configurations, the pads 12, 13, 14, 15, 17 can be adjustable. For example but without limitation, in some configurations, the pad or pads 12, 13, 14, 15, 17 can be pressurized by a fluid to change the resilience and/or hardness of the pad or pads 12, 13, 14, 15, 17.

Figure 10:
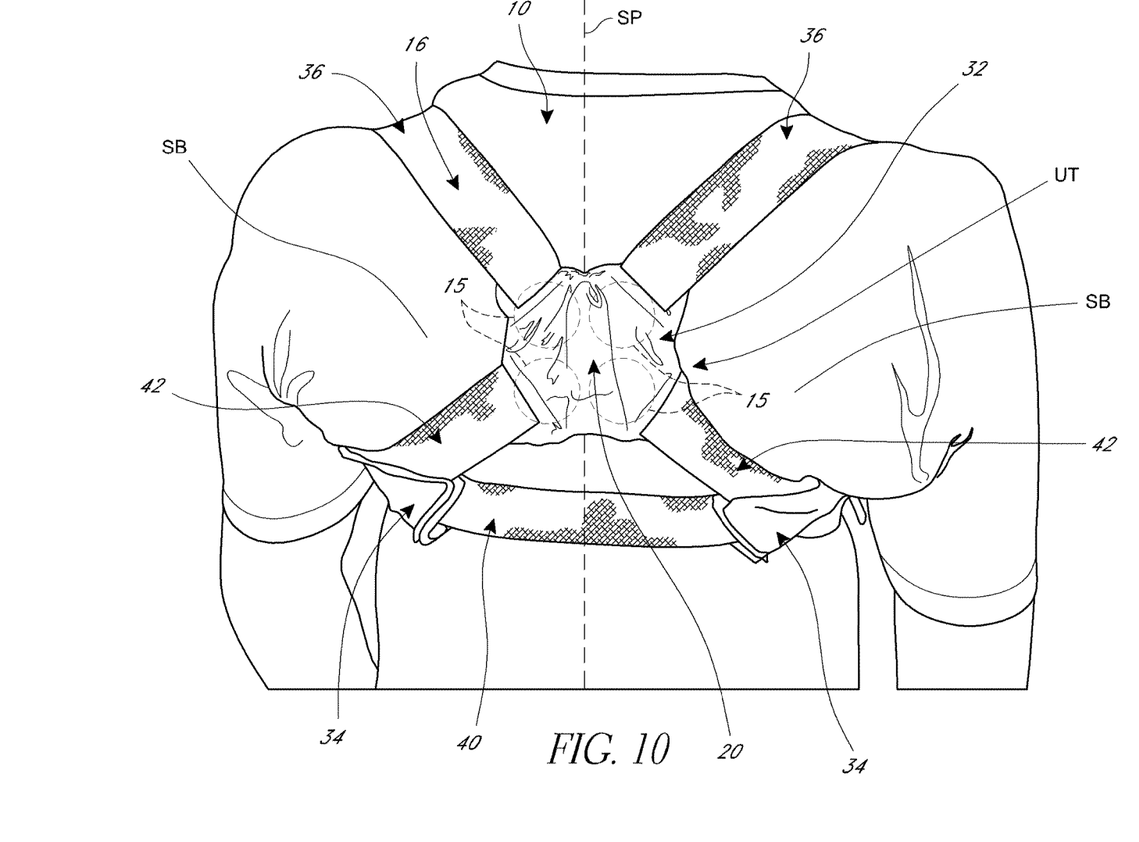
FIG. 10 is a rear view of the dorsal spine support device being worn with a plurality of pads positioned within a pouch.
Figure 11:
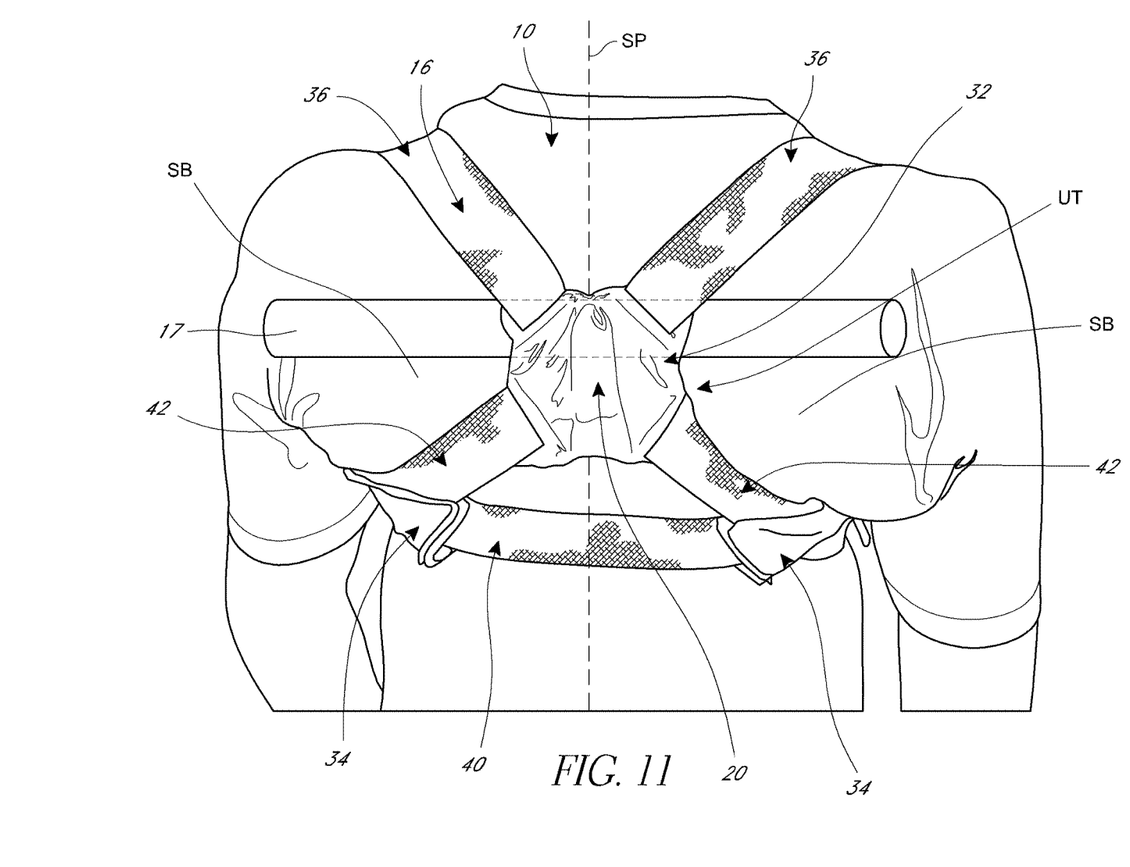
FIG. 11 is a rear view of the dorsal spine support device being worn with a laterally extending pad.

In some configurations, the pads can be configured to not touch the spine. In some configurations, the pads 13 can be designed to straddle the spine SP. In some such configurations, the pad 13 can be semi cylindrical or hemispherical with a recess 46 defined along a body facing surface 48. The recess can be sized and configured to accommodate a spine of the user. In some configurations, a plurality of pads 12, 13, 14, 15, 17 can be used and positioned such that they are positioned to each side of the spine of the user. For example, as shown in FIG. 10, two or four pads 15 can be positioned such that the pads 15 generally are disposed to each side of the spine of the user. In some configurations, the pads 12, 13, 14, 15, 17 can be configured to rest between the spine and the shoulder blades. In some configurations, such as that shown in FIG. 11, for example but without limitation, a pad 17 can extend laterally of the spine of the user and extend toward, overlap with, or project beyond the shoulder blades SB. In some such configurations, the pad can be generally cylindrical. In some such configuration, the pad 17 can be formed of a dowel rod. In some such configurations, the pad 17 can be formed of a wooden dowel rod. In some such configurations, the dowel can have a diameter of about 0.75 inch. In some such configurations, the pad 17 can be positioned within at least a portion of the channels 26 of the connector 32. When held in place, the strap 16 pushes the pads forward to help press the back forward without any direct contact on the spine SP The strap 16 is arranged and configured to wrap around a person's back, over the shoulders, and down such that the strap 16 crisscrosses between the shoulder blades SB. The strap 16 wraps around the ribs and the first end 28 of the strap 16 can be secured to the second end 30 of the strap 16 in front of the chest. By being so positioned, the strap 16 can pull the shoulders down and rearwards. By pulling the shoulders downs and rearwards, the strap 16 causes a movement that draws the shoulder blades SB forward. This action places a therapeutic pressure on the dorsal spine UT, which is the portion of the spine SP between the shoulder blades, by pushing it forward. This action also broadens and opens the chest. Opening the chest can create an effect of having the heart forward. The result of this combined action is improved upper body spinal posture. When the pad or pads 12, 13, 14, 15, 17 is used and the strap 16 is tightened, the pad or pads 12, 13, 14, 15, 17 acts as a fulcrum point between the shoulder blades SB, providing even greater pressure on the dorsal spine UT, similar to a massage. Thus, the pad or pads 12, 13, 14, 15, 17 can provide even greater pressure on the dorsal spine UT.

Figure 6:
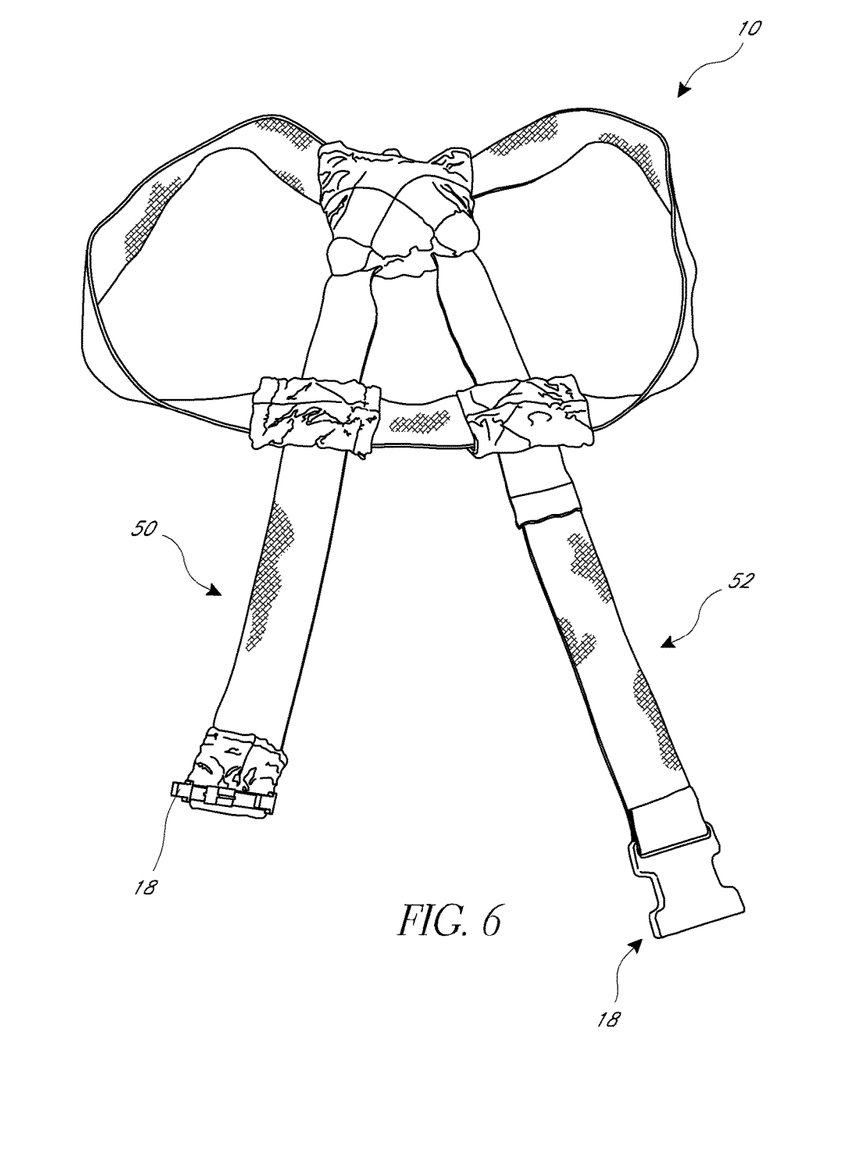
FIG. 6 is a rear view of another dorsal spine support device similar to that of FIG. 1 but with an extensible strap portion.

With reference now to FIG. 6, in some configurations, at least a portion 50 of the strap 16 is formed of an inextensible component while at least a portion 52 of the strap 16 is formed of a relatively more extensible component. The ability to take deep breaths, as well as regular, smooth breaths is very important. This is true during exercise, at work, and even at rest/meditation. Often certain poses or movements are performed or timed with either the inhale or the exhale for maximum benefit and control.

Figure 1:
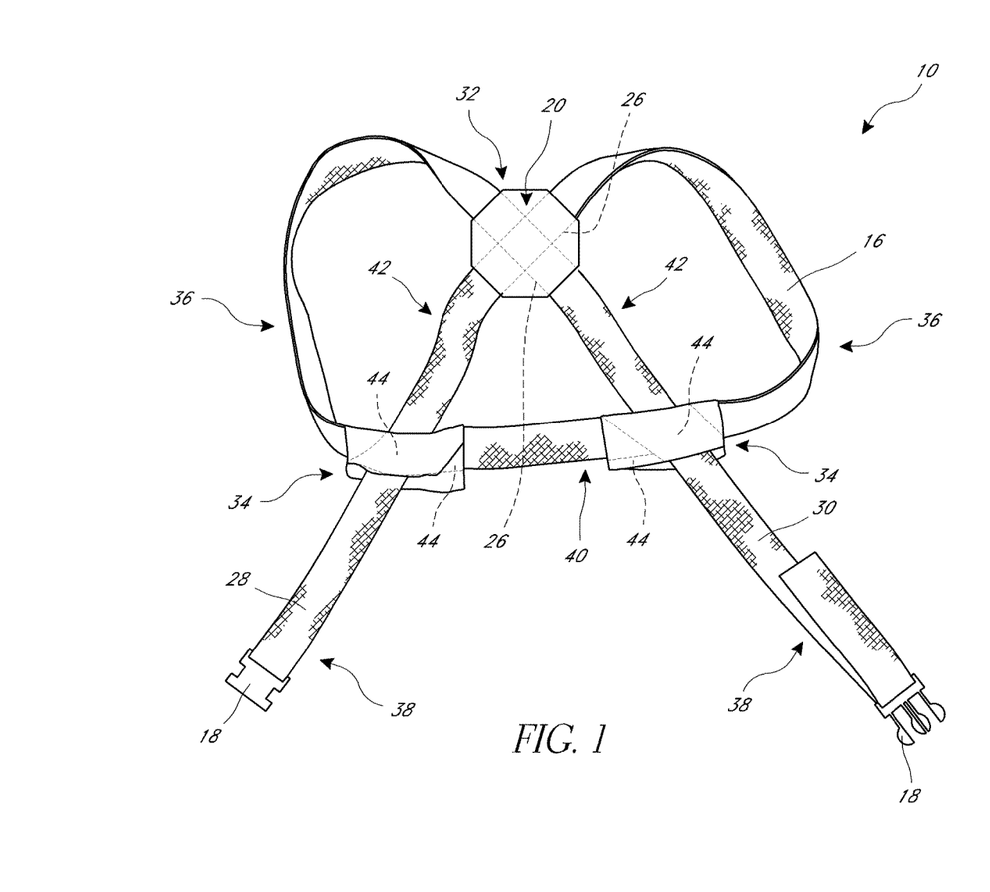
FIG. 1 is a rear view of a dorsal spine support device that is arranged and configured in accordance with certain features, aspects and advantages of the present invention.
Figure 2:
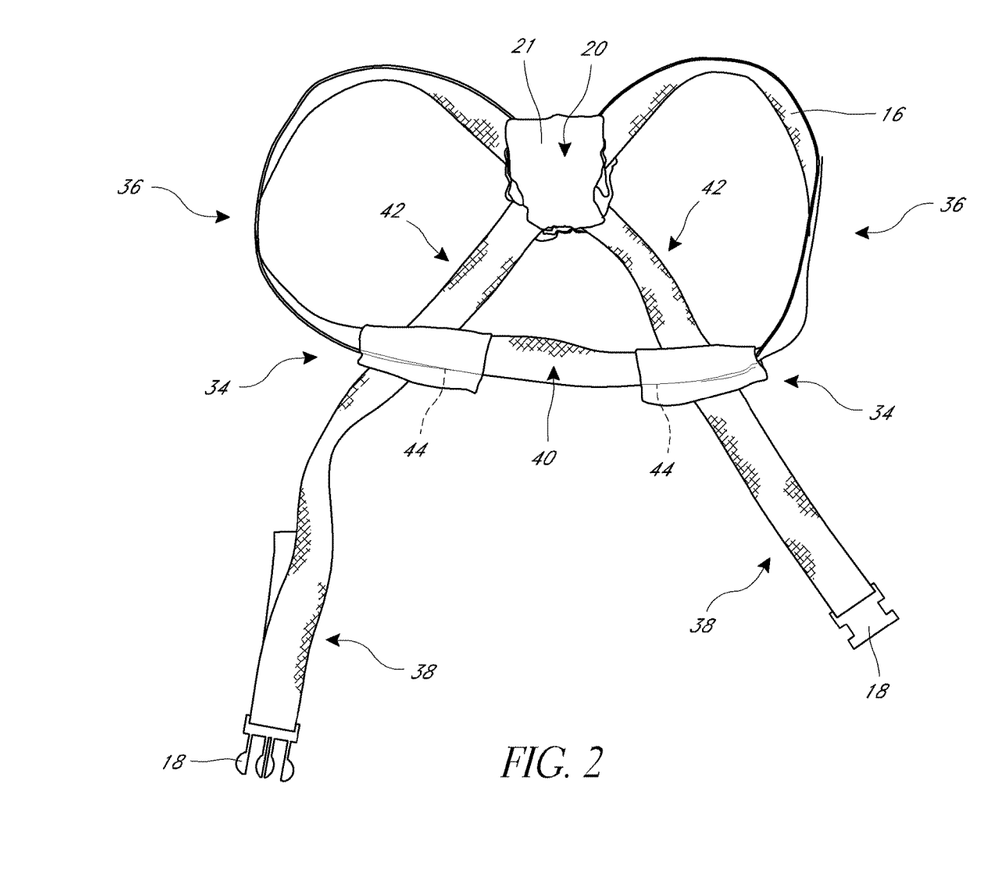
FIG. 2 is a front view of the dorsal spine support device of FIG. 1.

With the configuration of FIG. 1, it can be difficult to comfortably achieve the depth of breathing desired while having the dorsal spine device 10 tightened sufficiently to pull the shoulders down and back. In some configurations, the strap 16 extends around the front of the user's body at a location generally below the sternum. In such configurations, the user may feel the strap directly on or adjacent to the diaphragm. Through the use of the relatively more extensible portion 52, the dorsal strap device 10 is better able to accommodate the depth of breathing desired by some users.

In some configurations, the relatively more extensible portion 52 can be attached to one end of the relatively less extensible portion 50 (e.g., the less extensible strap). In some configurations, the relatively more extensible components can be attached between the relatively less extensible portion 50 and at least one portion of a buckle or other closure member 18. In some configurations, the relatively more extensible portion 52 connects the buckle or other closure member 18 to the relatively less extensible portion 50. In some configurations, two or more relatively more extensible portions 52 can be provided. In some configurations, the relatively more extensible portion or portions 52 can be configured to define at least a portion of the span of the strap 16 defined between the closure member 18 and the connectors 34. In some such configurations, the relatively more extensible portion is configured to extend around both sides of the user's body. In some such configurations, the relatively more extensible portion is configured to extend around only one side of the user's body. In some such configurations, the relatively more extensible portion 52 is not used on an adjustable side of the closure member 18.

It has been found that, when the relatively more extensible portion 52 has an appropriate level of elasticity, the user is better able to comfortably take deeper breaths while the balance of the strap 16 of the dorsal spine support device maintains a sufficient degree of inelasticity in the overall strap 16 to have a desired effect of pulling the shoulders down and back and pressing the chest open (or forward) through the forces applied in the upper dorsal spine region UT.

In some configurations, the relatively more extensible portion 52 features a banded elastic fabric material. In some such configurations, the banded elastic fabric comprises two layers with a finished length (e.g., between sewn seams) of between 5 inches and 8 inches. In some such configurations, a width of the relatively more extensible component matches a width of the relatively less extensible component of the strap 16. In some such configurations, the banded elastic fabric is formed of two layers (e.g., doubled over or two separate pieces). In some configurations, the banded elastic fabric has a thickness of 0.0675 inch (i.e., when doubled over or two separate layers, 0.125 inch).

The relatively more elastic portion 52 can have an amount of elasticity that allows the portion to experience a maximum of between 12.5% and 25% elongation under tensile loading. In some configurations, the relatively more elastic portion experiences a maximum stretch of between 18% and 19% elongation under tensile loading. The maximum percent elongation is determined by taking a base length of material and applying a tensile load. In some configurations, the tensile load is applied evenly over time. Thus, the maximum percent elongation can be calculated as (X−Y/Y)*100, where X is the elongated length (i.e., the length during force application) and Y is the base length (i.e., the length prior to force application). For example, if 2 inches is the base length and the elongated length is measured as 2.375 inches, then the percent elongation is ((2.375−2)/2)=18.8%. By way of comparison, the elastic waistband of an undergarment will experience about 62.5% elongation, the elastic of a men's nylon dress sock at the calf region will experience about 75% elongation, and the elastic of a men's athletic sock at the ankle region will experience about 75% elongation.

In some configurations, the dorsal spine support device can be supplied as a kit of components. The kit can comprise the strap 16 (with or without the relatively extensible portion), two relatively smaller criss-cross connectors 34 and one relatively larger criss-cross connector 32, a pouch (which be integrally formed as one unit with the connector 32), and one or more pads 12, 13, 14, 15, 17. In some configurations, the kit includes more than one pad shape, size or resilience within the one or more pads 12, 13, 14, 15, 17. In such configurations, the pads 12, 13, 14, 15, 17 can be interchangeable.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A dorsal spine support device comprising a support element consisting of a single strap,
the single strap intersecting itself in exactly three discrete locations, the single strap comprising a first end and a second end, the first end of the single strap being connectable to and disconnectable from the second end of the single strap;
a pouch comprising a first wall configured to contact a user in use and a second wall, the first wall comprising a body-facing surface, a third wall being positioned between the first wall and the second wall, a pocket being defined by the first wall and the third wall, four openings being defined between the second wall and the third wall with two discrete portions of the single strap passing through the four openings, the two discrete portions of the single strap that pass through the four openings defining an uppermost intersection point of the exactly three discrete locations such that the first wall is configured to be positioned between the single strap and the user in use, the pouch being adjustable in location relative to the two discrete portions of the single strap; and
the pocket being configured to receive a pad such that the pad is positioned between the two discrete portions of the single strap and the body of the user in use.

2. The dorsal spine support device of claim 1, wherein the pouch is removably connected to the single strap.

3. The dorsal spine support device of claim 2, wherein the pouch comprises one or more channels through which the single strap may pass.

4. The dorsal spine support device of claim 1 further comprising the pad that is sized and configured for insertion into the pocket.

5. The dorsal spine support device of claim 4, wherein the pad comprises a curved surface that is configured for contact with a body of a user.

6. The dorsal spine support device of claim 5, wherein the pad comprises a flat surface over which the single strap passes such that the pad will be positioned between the single strap and the body of the user.

7. The dorsal spine support device of claim 4, wherein the pad can have a soft, firm or very firm resilience.

8. The dorsal spine support device of claim 4, wherein the pad comprises two rounded surfaces arranged and configured to rest alongside a ridge of a spine of the body of the user.

9. The dorsal spine support device of claim 4, wherein the pad comprises a recess that allows the pad to straddle the spine of the body of the user.

10. The dorsal spine support device of claim 1, wherein the four openings define two channels that are on, along, or at least partially inside of the pouch.

11. The dorsal spine support device of claim 1, wherein the second wall is semi-permanently or permanently attached to the pocket that is defined by the first wall and the third wall.

12. The dorsal spine support device of claim 1, wherein the pouch comprises a pocket opening and the pocket opening being position only along an upper portion of the pouch.

13. The dorsal spine support device of claim 12, wherein the pocket opening is closable using one or more hook and loop fasteners.

14. The dorsal spine support device of claim 1, wherein each of the lower two of the exactly three discrete locations is defined by a crisscross strap connector.

15. The dorsal spine support device of claim 14, wherein each of the crisscross strap connectors allows the single strap to be adjusted relative to the crisscross strap connector along two non-aligned directions.

16. The dorsal spine support device of claim 15, wherein each crisscross strap connector defines two channels along which the strap is adjustable.

* * * * *